(12) United States Patent
Madlung et al.

(10) Patent No.: US 11,020,564 B2
(45) Date of Patent: Jun. 1, 2021

(54) CATHETER INSERTION AID (71) Applicant: DENTSPLY IH AB, Mölndal (SE)

(72) Inventors: Peter Madlung, Gothenburg (SE);
Martin Lovmar, Mölndal (SE);
Evelina Gustavsson, Onsala (SE)

(73) Assignee: DENTSPLY IH AB, Mölndal (SE)

( * ) Notice: Subject to any disclaimer, the term of this patent is extended or adjusted under 35 U.S.C. 154(b) by 386 days.

(21) Appl. No.: 15/783,735

(22) Filed: Oct. 13, 2017

(65) Prior Publication Data

US 2018/0104447 A1    Apr. 19, 2018

(30) Foreign Application Priority Data

Oct. 14, 2016    (EP) ..................... 16193874

(51) Int. Cl.
*A61M 25/01*    (2006.01)
*A61M 25/00*    (2006.01)

(52) U.S. Cl.
CPC .... *A61M 25/0113* (2013.01); *A61M 25/0045* (2013.01); *A61M 25/0111* (2013.01); *A61M 25/002* (2013.01); *A61M 2025/0046* (2013.01); *A61M 2205/0216* (2013.01); *A61M 2210/1096* (2013.01)

(58) Field of Classification Search
CPC .................. A61B 1/0014; B65D 25/32; B65D 2501/24936; B65D 2525/28; B65D 2525/289; A45F 2005/1006; A45F 2005/1013; A61M 5/321
See application file for complete search history.

(56) References Cited

U.S. PATENT DOCUMENTS 3,537,451 A * 11/1970 Beck ..................... A61M 25/06
604/165.03
3,574,306 A * 4/1971 Alden .................. A61M 25/02
604/162

(Continued)

FOREIGN PATENT DOCUMENTS

EP    0567029    10/1993
EP    1131022    8/2005

(Continued)

OTHER PUBLICATIONS

European Search Report for European Patent Application No. 16193874.1, dated Mar. 31, 2017 (8 pages).

*Primary Examiner* — Adam Marcetich
(74) *Attorney, Agent, or Firm* — Perkins Coie LLP (57) ABSTRACT

An insertion aid for catheter manipulation is disclosed. The insertion aid can be used for urinary catheters, such as hydrophilic urinary catheters for intermittent use. The insertion aid includes first and second plate-like arms arranged overlying each other and with a separation distance there between. The insertion aid also includes a resilient hinge connecting adjacent marginal edges of the plate-like arms together. At least one of the plate-like arms includes a groove on its clamping inner surface for holding a catheter shaft. The groove extends at least partly in the same direction as, and essentially parallel to, the resilient hinge, and is arranged at a distance both from the resilient hinge and from the marginal edge of the plate-like arm. Corresponding catheter set and catheter assembly are also disclosed.

32 Claims, 4 Drawing Sheets

(56) References Cited

U.S. PATENT DOCUMENTS

| | | | | |
|---|---|---|---|---|
| 3,598,118 | A * | 8/1971 | Warren | A61M 25/065 604/508 |
| 3,766,915 | A * | 10/1973 | Rychlik | A61M 25/06 604/161 |
| 3,853,130 | A | 12/1974 | Sheridan | |
| 3,993,081 | A * | 11/1976 | Cussell | A61M 16/0488 128/207.14 |
| 4,179,954 | A * | 12/1979 | Whalen | B67B 7/18 81/3.44 |
| 4,985,018 | A * | 1/1991 | Smith | A61M 25/0111 604/161 |
| 5,368,575 | A * | 11/1994 | Chang | A61M 25/02 128/912 |
| 5,382,239 | A * | 1/1995 | Orr | A61M 25/02 604/177 |
| 5,480,030 | A * | 1/1996 | Sweeney | B65D 33/1666 206/522 |
| 5,709,423 | A * | 1/1998 | Romero | A47G 21/10 294/16 |
| 5,827,239 | A * | 10/1998 | Dillon | A61M 25/0631 604/263 |
| 5,830,157 | A * | 11/1998 | Foote | A61M 25/0905 600/585 |
| 6,235,006 | B1 * | 5/2001 | Dillon | A61M 25/0631 604/162 |
| 6,263,761 | B1 * | 7/2001 | Ryder | B67B 7/04 7/151 |
| 6,554,802 | B1 * | 4/2003 | Pearson | A61M 25/02 604/165.03 |
| 6,616,635 | B1 * | 9/2003 | Bell | A61M 25/0631 604/192 |
| 8,801,065 | B1 * | 8/2014 | Jones | A45F 5/10 16/430 |
| 2003/0221858 | A1 * | 12/2003 | James | H02G 3/0487 174/93 |
| 2004/0073193 | A1 * | 4/2004 | Houser | A61M 25/09041 604/528 |
| 2005/0167999 | A1 * | 8/2005 | Beal | A61J 1/16 294/16 |
| 2005/0236853 | A1 * | 10/2005 | Demetroulakos | A47J 43/283 294/99.2 |
| 2007/0112378 | A1 * | 5/2007 | Sgobero | A45D 26/0066 606/210 |
| 2008/0097362 | A1 | 4/2008 | Mosler et al. | |
| 2009/0043287 | A1 * | 2/2009 | Mosler | A61M 25/013 604/544 |
| 2009/0209881 | A1 * | 8/2009 | Willcocks | A61B 10/007 600/573 |
| 2013/0231641 | A1 * | 9/2013 | Gustavsson | A61M 25/013 604/544 |
| 2014/0041092 | A1 * | 2/2014 | Ebbott | A41D 13/082 2/20 |
| 2016/0318196 | A1 * | 11/2016 | Reder | B67B 7/30 |

FOREIGN PATENT DOCUMENTS

| | | |
|---|---|---|
| EP | 2106821 | 10/2009 |
| WO | 2011129780 | 10/2011 |

\* cited by examiner

CATHETER INSERTION AID

CROSS-REFERENCE TO RELATED APPLICATIONS

This patent document claims the benefits and priority of European Patent Convention Application No. 16193874.1, filed on Oct. 14, 2016, which is incorporated herein by reference in its entirety.

FIELD OF DISCLOSED TECHNOLOGY

The disclosed technology is related to a catheter insertion aid, and in particular a urinary catheter insertion aid, to facilitate handling of the catheter. It is also related to a corresponding catheter set.

BACKGROUND

Catheters, such as urinary catheters, and in particular catheters having hydrophilic coatings, are relatively difficult to handle, since the surface before application and use is very slippery. Further, direct contact with the insertable part of the catheter should preferably be avoided, in order to avoid contamination of the catheter, and thereby minimize the risk of e.g. urinary tract infections. Still further, many users of intermittent urinary catheterization are disabled or have poor dexterity for other reasons, and consequently, there is also for this ground a need for means for making manipulation and insertion of catheters easier, cleaner and safer.

To overcome these problems, many alternative insertion aids have been proposed during the last years. For example, EP 1 131 022 discloses an applicator which is formed as an integrated and detachable hose member arranged in the catheter package in which the catheter is arranged. However, as a consequence, the catheter package becomes relatively complicated and costly, and also, the operation of using this catheter assembly is relatively cumbersome.

Further, EP 2 106 821 discloses a catheter assembly in which an insertion aid is arranged as a tubular part arranged over the connector part of the catheter. Upon use, the tubular insertion aid may be loosened from its position on the connector, and moved along the catheter shaft. However, this solution is also relatively complicated and costly, since assembly of the product is quite complicated, and adequate connection of the tubular part on the connector and at the same time easy detachment by the user is difficult to achieve.

There is therefore still a need for an insertion aid which is easier, safer and/or cleaner to use and/or easier and more cost-efficient to produce.

SUMMARY

There is therefore an object of the disclosed embodiments to provide a catheter insertion aid, a catheter set and a catheter assembly that at least partly overcome the above-discussed problems of the prior art.

In some embodiments, this object is achieved by means of a catheter insertion aid, a catheter set and a catheter assembly according to the enclosed claims.

According to a first aspect of the disclosed technology, there is provided an insertion aid for catheter manipulation, comprising first and second plate-like arms arranged overlying each other and with a separation distance there between, and a resilient hinge connecting adjacent marginal edges of said plate-like arms together, wherein at least one of said plate-like arms is provided with a groove on a clamping inner surface thereof for holding a catheter shaft, the groove extending at least partly in the same direction as, and preferably essentially parallel to, said resilient hinge, and arranged at a distance both from said resilient hinge and from the marginal edge of said plate-like arm being opposite to said resilient hinge.

The construction with plate-like arms extending from a resilient hinge provides a clamping arrangement which is very simple to use, also for persons having reduced dexterity. Clamping can easily be obtained by pressing the plate-like arms towards each other. This can be made by pressing the plate-like arms together by use of two fingers, by means of pressing one or several fingers towards the palm, by use of two hands, by pressing on only one of the plate-like arms while the other is in contact with another part of the body or an external structure, and the like. Thus, the insertion aid provides numerous simple handling possibilities, which is particularly useful for users having reduced dexterity.

Further, the arrangement of a groove in one or both the clamping surfaces of the plate-like members, the catheter is maintained in a correct position during operation, avoiding the risk of the catheter inadvertently falling out or being misplaced.

Further, the arrangement of the groove at a distance both from the resilient hinge and from the marginal edge of the plate-like arm(s) opposite to the resilient hinge is very efficient. The distance between the groove and the resilient hinge reduces the pressure necessary to apply to the plate-like arms to adequately clamp the catheter during use. At the same time, the distance between the groove and the opposite marginal edge of the plate-like arm(s) provides a lever when applying the pressure, thereby reducing the required exerted force on the plate-like arms. Thus, by applying the compression force at or in the vicinity of the marginal edges opposite to the resilient hinge, a relatively high clamping pressure can be obtained with a very limited force. This makes use of the insertion aid very simple, and is particularly useful for users having reduced dexterity.

At a certain, relatively limited, applied force, the marginal edges of the plate-like arms will also come into contact with each other, thereby preventing further clamping of the catheter tube, regardless of whether a higher applied force is applied or not. This means that well-defined clamping force is obtained at almost all times, more or less regardless of how high or low the applied clamping force is, and thereby alleviating the user's need of fine motor ability.

At the same time, release of the clamping is also simple. By simply reducing the compression force being applied on the plate-like arms, the clamping pressure is immediately reduced, allowing the insertion aid to be moved in relation to the catheter, in order e.g. to be repositioned at another position along the catheter shaft.

Thus, the insertion aid provides a simple operation, which is yet highly effective to maintain the catheter in safely clamped disposition when this is desired, and which makes release and repositioning of the insertion aid simple and efficient.

Use of the insertion aid thereby avoids the need to directly touch the catheter, and in particular the insertable part of the catheter. This reduces the risk of contaminating the insertable part of the catheter prior to insertion. It may also be used to manipulate the catheter during and after withdrawal, thereby avoiding the risk of the user being contaminated by the used catheter. This contamination free handling of the catheter reduces the risk of urinary tract infections and the like.

The new insertion aid also lends itself well for efficient manufacturing and assembly, both when performed manually as well as in automated or semi-automated production. The insertion aid in itself may e.g. be injection molded or extruded. Further, the jaw-like configuration enables simple and efficient application of the insertion aid on the catheter both during manufacturing and during subsequent use. This also makes packaging of the catheter and the insertion aid easier. Thus, the insertion aid may hereby be located over the catheter already during manufacturing, or be arranged separated from the catheter in a catheter assembly, or even be provided separate from the catheter package. At the same time, attachment and detachment of the insertion aid is made very simple, even for users with reduced dexterity.

Further, the insertion aid is very versatile, and the same design and size can be used for many types of different catheters, and for many different catheter sizes.

The groove preferably extends over the entire length of the plate-like arm on which it is arranged. However, in some embodiments the groove may alternatively be shorter than the length of the plate-like member, so that it only extends over part of the plate-like arm on which it is arranged. For example, if the distance between the plate-like arms increases towards the ends, the groove need not necessarily extend into the slanted or beveled portions of the plate-like arm(s), or may extend only partly into these portions. Further, the depth of the groove may also gradually decrease in such slanted/beveled portions.

The groove is preferably smoothly curved from one longitudinal side to the other, e.g. forming a cross-sectional shape of a semi-circle or a lesser part of a circle. However, the cross-sectional shape may also be oval, elliptic or the like.

The width of the groove is preferably about the same size as the diameter of the catheter shaft of the catheter it is intended for. The width is preferably in the range of 2-10 mm, and most preferably in the range 3-6 mm. Similarly, the depth of the groove is preferably about half the width of the groove, and is preferably in the range of 1-5 mm, and most preferably in the range 1.5-3 mm.

The groove may be arranged closer to the marginal edge of the plate-like arm being opposite to the resilient hinge than to the resilient hinge. It is also possible to arrange the groove essentially in the middle of the plate-like arms, i.e. with essentially the same distance to both the resilient hinge and the opposite marginal edge.

However, in one embodiment the groove is arranged closer to the resilient hinge than to the marginal edge of said plate-like arm being opposite to said resilient hinge. In particular, it is preferred that the distance between the groove and the resilient hinge is 25-75% of the distance between groove and the marginal edge of said plate-like arm being opposite to said resilient hinge, and preferably 30-70%, and most preferably 40-60%. Put differently, it is preferred that the distance between the groove and the marginal edge of said plate-like arm being opposite to said resilient hinge is 1.3-4 times longer than the distance between the groove and the resilient hinge, and preferably 1.3-3.3 times longer, and most preferably 1.7-2.5 times longer. Hereby, relatively long levers are provided, providing a very good balance between the clamping force needed to hold the catheter in place, the force needed to compress the plate-like arms, and the distance the plate-like arms need to be moved towards each other.

In one embodiment, both of said plate-like arms are provided with the groove on a clamping inner surface thereof for holding a catheter shaft, the grooves being arranged overlying each other, i.e. opposite to each other at the same, or about the same, distance from the hinge. Hereby, the catheter is even better maintained in the adequate, intended position during use, avoiding the risk of the catheter inadvertently falling out or being misplaced even further.

The insertion aid preferably has an length in the direction of the resilient hinge which is longer than the width perpendicular to the resilient hinge, thereby forming an elongate shape, and preferably at least 50% longer, and most preferably at least 100% longer. Hereby, relatively large gripping areas are formed, allowing e.g. the user to apply force to the plate-like arms by use of several fingers or even the entire hand and the like, without the risk of inadvertently touching the catheter. It also makes it easier to apply sufficient force, in particular for users having reduced dexterity. Preferably, the insertion aid is elongate in the direction of the groove, and wherein the length is preferably in the range of 4-10 cm, and preferably 5-9 cm, and most preferably 6-8 cm. Thus, the length is preferably about the same as the width of a palm. However, in some embodiments, the insertion aid may alternatively be of the same size in both length and width direction, or even have a width exceeding the length.

It is possible to let the groove(s) extend in a slightly slanted direction compared to the resilient hinge. However, preferably, the groove and the resilient hinge extend along straight, parallel lines.

The resilient hinge may be arranged to exert a clamping force onto a catheter arranged in the insertion aid also when in an non-activated state, i.e. in a state where the user does not exert an external clamping pressure. Hereby, the insertion aid will apply a certain, limited clamping force on the catheter also when no additional clamping force is applied. Hereby, the insertion aid will stay in place over the catheter at all times, unless it is deliberately moved by the user. This facilitates use, since the user may release insertion aid during use, without the risk of the insertion aid falling down and the like. It also facilitates manufacturing, since the insertion aid can hereby be arranged on the catheter already during manufacturing, and then remain in place during packaging, sterilization, handling, storage, etc. In case of e.g. a hydrophilic catheter, it will also remain in place during activation and preparation for use. The insertion aid may also remain in place e.g. when the catheter is removed from its package.

The insertion aid may also comprise inward protrusions or recessions which may be engaged with a recession or protrusion or the like in the catheter and/or catheter connector, thereby securely connecting the insertion aid to the catheter. Such a connection may form a weak mechanical interlocking, which maintains the insertion aid in an intended stored position. At the same time, disassembling of the insertion aid is simple, since the insertion aid can easily be pulled out of this weakly locked state, thereby allowing clean and safe maneuvering of insertion aid over the catheter during insertion into the intended human cavity.

Further, the insertion aid will hereby always be kept securely in place before it is removed and used as an insertion aid.

The insertion aid is preferably arranged overlying or adjacent the connector of the catheter. Thus, if the user does not need an insertion aid for manipulation of the catheter, the insertion aid can be allowed to remain in its non-released state during the entire use. Even in this way of using the catheter, where the insertion aid remains non-detached, the insertion aid is to advantage, since it hereby provides an enlarged gripping portion for the catheter, which makes insertion and withdrawal of the catheter easier, especially for users with reduced dexterity.

By "connector" is in this application meant the rearward end of the catheter, which may be used to connect the catheter to external tubing, a urine collection bag, or the like. However, notably the connector need not necessarily be connected to anything, but may also in itself serve as a discharge end. Further, the connector may have a specific geometrical shape, such as being at least partly funnel shaped, having a frusto-conical shape, being flared, or the like. However, in the most general sense, the connector need not have a geometrical shape distinguishing it from the catheter tube, and may e.g. in its simplest form be the integrated rearward part of the catheter tube. Further, the connector may be a separate component, which is connected to the catheter tube during manufacturing, or may be formed as a unified, integral part of the catheter tube.

The plate-like arms are preferably curved or bent away from each other along at least part of the marginal edge. Hereby, an enlarged opening is formed, facilitating arrangement of the insertion aid over the catheter, both during production and during subsequent use.

The insertion aid is preferably formed as a clip, wherein the plate-like arms form a receiving mouth at the ends opposite to the resilient hinge.

The plate-like arm may be provided with a slanted or beveled internal surface in the vicinity of the ends of the groove. This makes the edges smoother, thereby minimizing the risk of damaging the catheter when the insertion aid is moved along the catheter shaft. This is of particular advantage when the catheter is provided with a coating, such as a hydrophilic coating, thereby limiting the risk of the coating being deteriorated by such movement.

At least one of the plate-like arms may be provided with protrusions on an external surface thereof, and preferably both said plate-like arms, and most preferably protrusions extending in a direction perpendicular to the groove. Hereby, gripping of the plate-like arms, for holding and manipulating the insertion aid, and for applying the clamping force, is facilitated. The protrusions may be formed by at least one of outward protrusion lines, point like protrusions and corrugations. However other means for facilitating gripping may also be used, such as providing an increased surface texture, e.g. in the form of embossment and perforations.

At least one of the plate-like arms may be provided with protrusions on an internal surface thereof, and preferably both said plate-like arms, and most preferably protrusions extending in a direction perpendicular to the groove. Hereby, the friction between the catheter and the insertion aid is increased, thereby limiting the clamping force necessary to maintain the catheter in position during maneuvering and the like. The protrusions may be formed by at least one of outward protrusion lines, point like protrusions and corrugations. However other means for increasing friction may also be used, such as providing an increased surface texture, e.g. in the form of embossment and perforations.

The insertion aid may be monolithic and made of a plastics material, and preferably a thermoplastic and/or thermosetting plastic material, and most preferably a thermoplastic elastomer.

The resilient hinge is preferably provided with at least one cavity or opening arranged between the plate-like arms. Hereby, the same material can be used in both the resilient hinge and the plate-like arms, and still making the resilient hinge more flexible than the plate-like arms. Also, such cavities and openings reduce the amount of material in the insertion aid, thereby lowering weight and manufacturing costs.

Further, the provisions of such cavities or openings also makes the insertion aid flexible in a longitudinal direction, so that the insertion aid can be bent also in the longitudinal direction by compression forces applied by the user. Hereby, the catheter will be held even more strongly in place during use.

According to another aspect of the disclosed technology there is provided a catheter set comprising a catheter and the insertion aid as discussed above, wherein the catheter comprises a forward insertion part and a rearward connector part, wherein, in a storage position, the insertion aid is arranged over the connector part of the catheter so that the insertion aid detachably connects the insertion aid to the catheter.

By means of this aspect of the disclosed technology, similar advantages and possible additional features as discussed above in relation to the first aspect of the disclosed technology are obtainable.

The catheter is preferably a hydrophilic catheter, wherein the forward insertion part is at least partly provided with a hydrophilic material exhibiting low-friction surface properties when wetted. The hydrophilic material is preferably arranged at least on an insertable length of the catheter.

Further, the catheter is preferably a urinary catheter, and preferably a urinary catheter for intermittent use.

The insertion aid is preferably made of material which is more rigid than the catheter shaft.

According to another aspect of the disclosed technology there is provided a catheter assembly comprising a catheter set as discussed above and a package enclosing said catheter set. By means of this aspect of the disclosed technology, similar advantages and possible additional features as discussed above in relation to the first aspect of the disclosed technology are obtainable.

These and other aspects of the disclosed technology will be apparent from and elucidated with reference to the embodiments described hereinafter.

BRIEF DESCRIPTION OF THE DRAWINGS

For exemplifying purposes, the disclosed technology will be described in closer detail in the following with reference to embodiments thereof illustrated in the attached drawings, wherein.

DETAILED DESCRIPTION OF PREFERRED EMBODIMENTS

In the following detailed description, preferred embodiments of the disclosed technology will be described. However, it is to be understood that features of the different embodiments are exchangeable between the embodiments and may be combined in different ways. It may also be noted that, for the sake of clarity, the dimensions of certain components illustrated in the drawings may differ from the corresponding dimensions in real-life implementations. Even though in the following description, numerous specific details are set forth to provide a more thorough understanding of the disclosed technology, it will be apparent to one skilled in the art that the disclosed technology may be practiced without these specific details. In other instances, well known constructions or functions are not described in detail, so as not to obscure the disclosed technology.

The following discussion is in particular concerned with an insertion aid for use with hydrophilic urinary catheters for intermittent use. However, the disclosed technology can also be used in relation to other types of urinary catheters, or other types of catheters in general.

An insertion aid according to an exemplary embodiment will first be discussed with reference to FIG. 1. The insertion aid 1 comprises first and second plate-like arms 11 arranged overlying each other and with a separation distance therebetween. The arms are connected together at one longitudinal side through a resilient hinge 12, thus connecting adjacent marginal edges of the plate-like arms together. Further, at least one of the plate-like arms 11 is provided with a groove 13. In this example, both arms are provided with such grooves 13, wherein the grooves are arranged overlying each other, at the same distance from the hinge 12. The grooves 13 extend at least partly in the same direction as, and preferably essentially parallel to, the resilient hinge 12, and are arranged at a distance both from the resilient hinge and from the marginal edges 14 of the plate-like arm being opposite to the resilient hinge 12. The grooves are provided on a clamping inner surface of the arms, for holding a catheter shaft, as will be discussed in more detail in the following.

The grooves may be centrally arranged, at the same or about the same distance from both the resilient hinge 12 and the marginal edges 14. The grooves may alternatively be arranged closer to the marginal edges 14. However, preferably, the grooves are, as also shown in FIG. 1, arranged closer to the resilient hinge 12 than to the marginal edges 14. For example, the distance between the groove and the resilient hinge 12 may be 25-75% of the distance between groove and the marginal edge 14, such as 30-70%, or such as 40-60%.

The insertion aid may be elongate, and preferably has a length extension in the direction of the resilient hinge which is longer than the width extension perpendicular to the resilient hinge, and preferably at least 50% longer, and most preferably at least 100% longer. The length is preferably in the range of 4-10 cm, and preferably 5-9 cm, and most preferably 6-8 cm. Thus, the length is preferably about the same as the width of a palm.

The marginal edges 14 of the arms being arranged opposite to the resilient hinge 12 forms an insertion opening, allowing the insertion aid to be assembled onto a catheter, by pushing the insertion aid laterally over the catheter shaft. To facilitate this, the arms 11 may be arranged to enlarge the opening. In the example of FIG. 1, the arms are outwardly slightly curved, so that the marginal edges 14 are to some extent directed away from each other. Hereby, an enlarged opening is formed, facilitating arrangement of the insertion aid over the catheter, both during production and during subsequent use.

The resilient hinge allows arms to be moved towards each other when a compression force is applied to the arms, and also is resilient so that the arms are moved back again when the compression force is released. In the illustrative example of FIG. 1, the resilient hinge is formed as an outwardly curved sidewall, extending between the arms.

Figure 2:
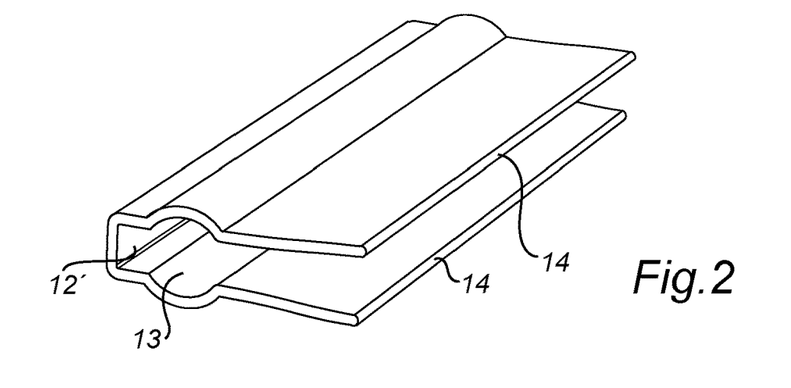
FIG. 2 is a side view in perspective of an insertion aid according to a second embodiment of the present disclosed technology.

However, the resilient hinge 12' may also be arranged as a relatively flat side wall, as illustrated in the embodiment of FIG. 2.

In the embodiment of FIG. 2, the enlarged opening formed by the marginal edges 14 is also not formed by providing a curvature in the arms. Instead, the arms are here essentially flat in the vicinity of the marginal edges 14, but angled in relation to each other, so that the distance between the arms gradually increases from the grooves and in the direction towards the marginal edges 14.

Figure 3:
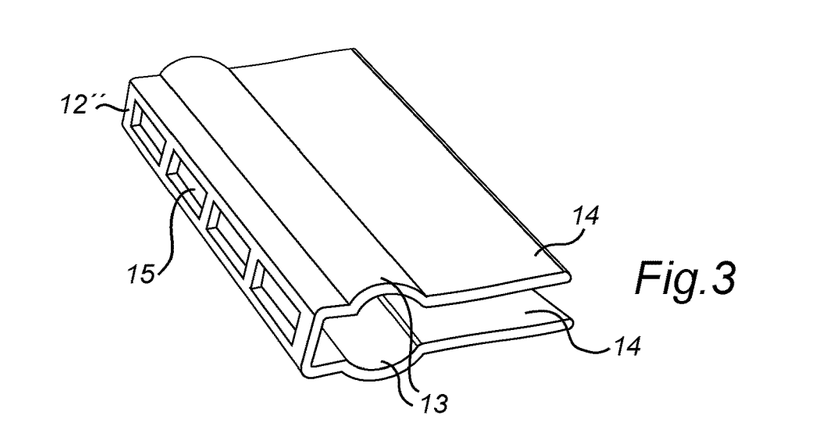
FIG. 3 is a side view in perspective of an insertion aid according to a third embodiment of the present disclosed technology.

Still further, the side wall of the resilient hinge may also be provided with at least one cavity or opening arranged between the plate-like arms, in order to increase flexibility and reduce material costs. Such an embodiment is illustrated in FIG. 3, where four cut-out openings 15 are formed in the resilient hinge 12", here being provided as a flat sidewall. However, more or fewer openings may also be used, and may also have other shapes than rectangular, such as circular, oval or the like. Further, instead of openings extending through the entire wall thickness, as in the illustrative example of FIG. 3, cavities of less depth may be used, such as holes, grooves or the like, penetrating only through part of the sidewall thickness.

In the embodiment of FIG. 3, an example is further provided of an insertion aid which does not form an enlarged opening opposite to the resilient hinge. Instead, the arms are here essentially parallel to each other from the grooves 13 to the marginal edges 14.

Figure 4:
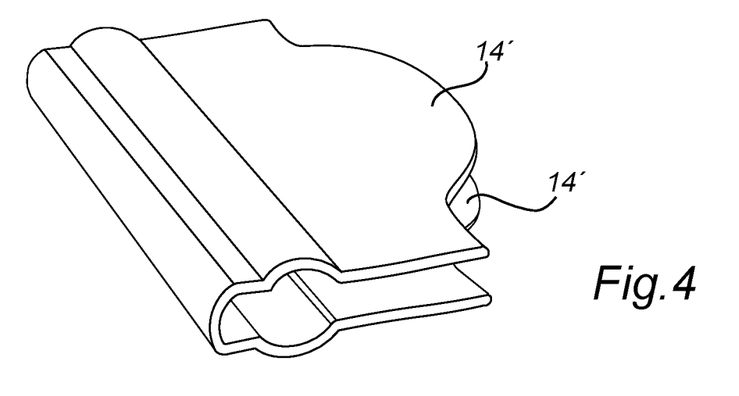
FIG. 4 is a side view in perspective of an insertion aid according to a fourth embodiment of the present disclosed technology.

Various arrangements may also be provided to facilitate application of compression forces to the arms to bring them closer towards each other. One such example is provided in the embodiment of FIG. 4, in which the marginal edges 14' are provided with centrally arranged and outwardly protruding tab areas. Hereby, an increased gripping area is provided. The tab areas shown in FIG. 4 are formed as rounded tongues extending out from the plate-like arms, and monolithically integrated with the plate-like arms. However, the protruding tab areas may alternatively be formed as separate parts, fixedly attached to the plate-like arms by e.g. welding, adhesion or the like. Further, it is also possible to have the protruding tab areas extending in a forward and/or backward direction, so that the tab areas at least partly extend past the marginal edge(s) of the plate-like arms in the length direction. The tab areas may hereby be e.g. in the shape of a mushroom, extending past the marginal edges in both direction, or in the shape of a hook, extending past the marginal edge in only one direction.

In the embodiments discussed so far, the distance between the arms is essentially constant when seen in any longitudinal cross section extending parallel to the resilient hinge.

Figure 5A:
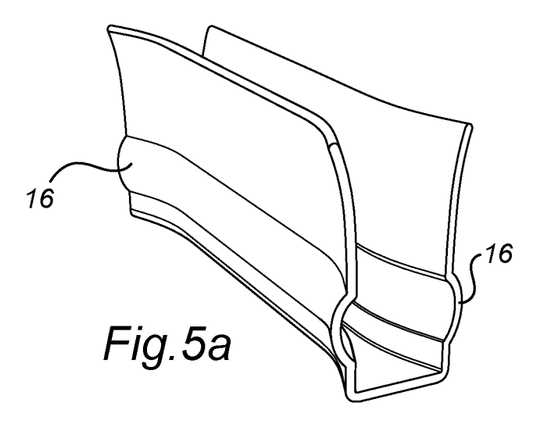
FIGS. 5a and 5b are a perspective side view and top view, respectively, of an insertion aid according to a fifth embodiment of the present disclosed technology.
Figure 5B:
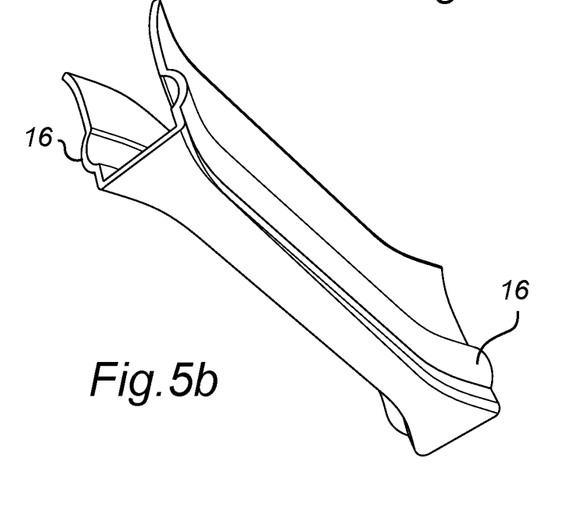

However, it is also possible to provide a varying distance between the arms along one or several such cross-sections. For example, it is possible to provide the plate-like arms with a slanted or beveled internal surface in the vicinity of the ends of the grooves. This makes the edges smoother, thereby minimizing the risk of damaging the catheter when the insertion aid is moved along the catheter shaft. Such an embodiment is shown in FIGS. 5a and 5b, where the arms in the vicinity of the marginal edges 16 of the arms directed perpendicular to the resilient hinge are curved outwardly, so that the marginal edges 16 are to some extent directed away from each other. Hereby, enlarged openings are formed at the lateral sides of the insertion aid. Such enlarged openings may be applied only to the lateral sides, and not to the longitudinal side opposite to the resilient hinge. However, in the illustrative example of FIG. 5, the longitudinal side is also provided with an enlarged opening, formed by outwardly curved arms, in the same way as discussed previously in relation to FIG. 1.

Figure 6:
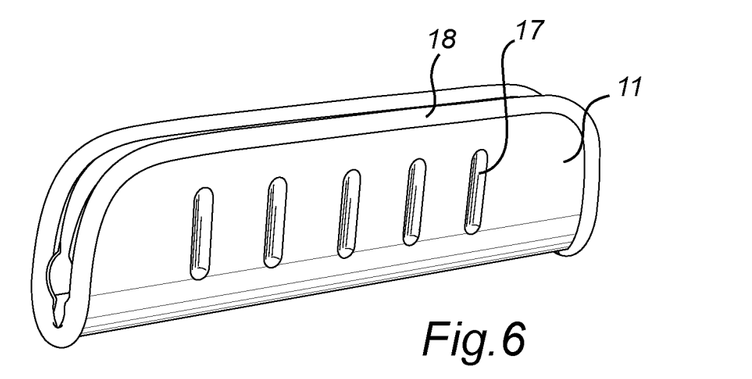
FIG. 6 is a side view in perspective of an insertion aid according to a sixth embodiment of the present disclosed technology.

In the embodiment of FIG. 6, the insertion aid has been provided with rounded corners. Further, protrusions have been provided on the external sides of the plate-like arms 11. More specifically, a number of protrusion lines 17 have been provided distributed centrally on the arms, and each extending in a direction generally perpendicular to the groove and the resilient hinge. In addition a protrusion line 18 running along the outer edges of the arms is provided. Due to these protrusions, gripping of the plate-like arms, for holding and manipulating the insertion aid, and for applying the clamping force, is facilitated. However, many other types of protrusions may be used in addition or instead of these protrusions. For example, point like protrusions and corrugations may be used. Other means for facilitating gripping may also be used, such as providing an increased surface texture, e.g. in the form of embossment and perforations.

Figure 7:
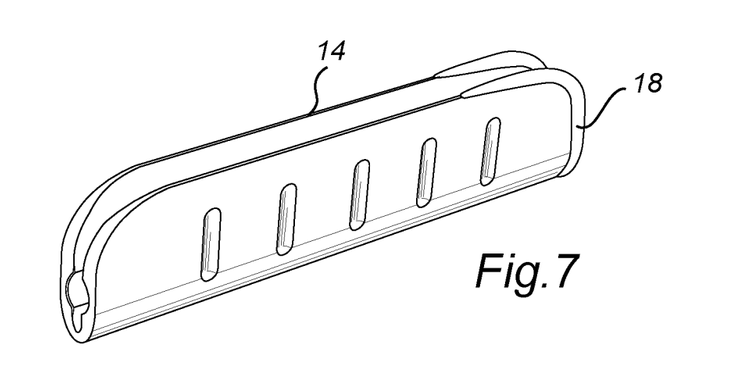
FIG. 7 is a side view in perspective of an insertion aid according to a seventh embodiment of the present disclosed technology.

The protrusion line 18 need not extend over all marginal edges of the two arms, as in the example of FIG. 6. Instead, one or several shorter protrusion line(s) may be arranged at or close to the edges. One such embodiment is illustrated in FIG. 7, in which the protrusion line 18 only extends over a lateral marginal edge, and a short distance into the longitudinal marginal edge.

Figure 1:
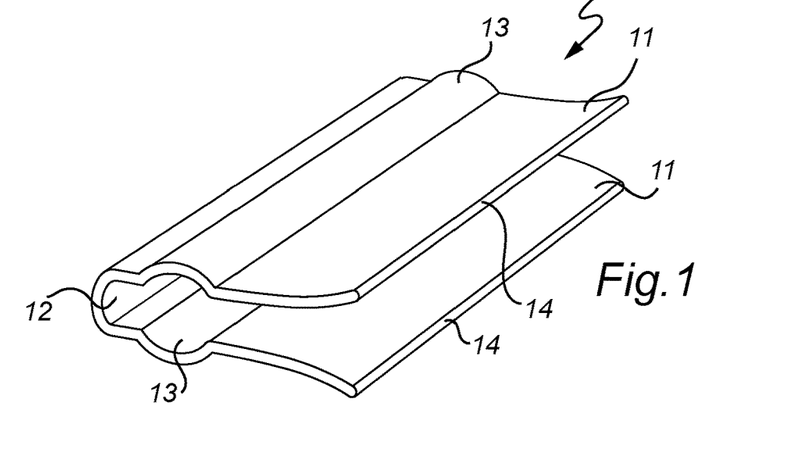
FIG. 1 is a side view in perspective of an insertion aid according to an embodiment of the present disclosed technology.

Further, instead of, or in addition, to forming an enlarged longitudinal opening by providing curved and/or angled plate-like arms, as discussed in the foregoing in relation to FIGS. 1 and 2, such an enlarged opening may be formed by beveled surfaces forming tapering ends towards the longitudinal marginal ends. Such an embodiment is also illustrated in FIG. 7. Hereby, the thickness of the plate-like arms gradually decreases towards the longitudinal marginal edges 14, thereby providing an enlarged opening. This tapering may extend over almost the entire plate-like arms from the grooves to the marginal edges 14. However, alternatively, the tapering may be provided on only a limited part of the arms being closest to the marginal edges. Such an embodiment is illustrated in FIG. 8.

Figure 8:
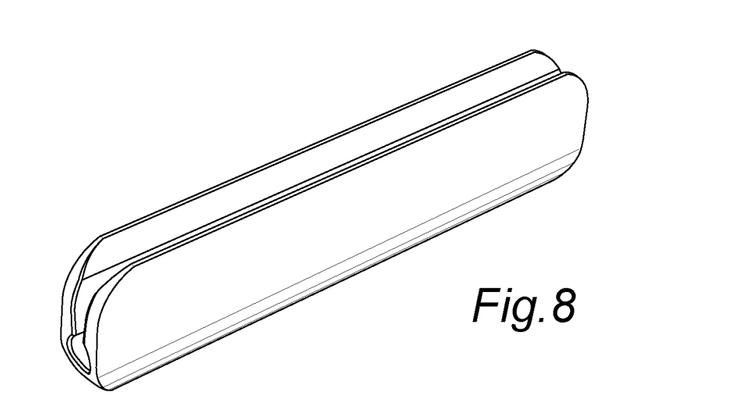
FIG. 8 is a side view in perspective of an insertion aid according to an eighth embodiment of the present disclosed technology.

Further, in the embodiment of FIG. 8, the distance between the grooves and the resilient hinge has been limited, so that the grooves are arranged very close to the resilient hinge.

Protrusions or the like (not shown) may also be provided on one or several of the internal surfaces of the plate-like arms, and preferably on internal surfaces of both said plate-like arms. Such protrusions may e.g. extend in a direction perpendicular to the groove. Hereby, the friction between the catheter and the insertion aid is increased, thereby limiting the clamping force necessary to maintain the catheter in position during maneuvering and the like. The protrusions may be formed as protrusion lines, but may alternatively be formed by point like protrusions and the like. Further, similar effects may be obtained by corrugations, by providing an increased surface texture, e.g. in the form of embossment and perforations, and the like.

The insertion aid may be formed by many different types of plastic materials, and in various ways. It may be formed by two or more different materials, e.g. one material for forming the resilient hinge, and another material for forming the plate-like arms. However, preferably, the entire insertion aid is formed by one and the same material. Preferably, the insertion aid is formed as a monolithic piece. Further, the plastic material is preferably a thermoplastic and/or thermosetting plastic material, and most preferably a thermoplastic elastomer. In one embodiment, the tubular insertion aid may be made of thermoplastic elastomer, such as the commercially available Dryflex® or LDPE. However, other materials are also feasible. For example, the material may be one or several of: a polymer material, such as polyurethanes, thermoplastic rubbers, polyvinylchloride, other vinyl polymers, polyesters, polyether block amid, polypropene, polyethen polyamide and styren-ethen/butadiene-styren copolymer, polyacrylates and polysiloxanes.

The insertion aid may be formed by injection molding. However, other manufacturing methods may also be employed. For example, the insertion aid may be formed by extrusion. In particular, embodiments where the lateral cross-section is essentially uniform along the length of the insertion aid are well-suited for extrusion, such as the embodiments discussed above in relation to FIGS. 1, 2 and 8.

The insertion aid may be provided as a separate component, e.g. arranged in a sterile package. However, preferably the insertion aid is arranged in a package together with the catheter. In this case, the insertion aid be arranged loosely within the package. However, preferably, the insertion aid is assembled on the catheter already during manufacture.

The catheter is preferably a hydrophilic catheter, having a hydrophilic exterior surface exhibiting a low-friction when wetted. The package may also comprise a wetting liquid, either in contact with the catheter, thereby maintaining the hydrophilic surface wetted and activated during storage, or in a separate compartment, to be released prior to use for activation of the catheter.

The resilient hinge may be arranged to exert a clamping force onto a catheter arranged in the insertion aid when in an unbiased state. Hereby, the insertion aid will apply a certain, limited clamping force on the catheter also when no additional clamping force is applied. Hereby, the insertion aid will stay in place over the catheter at all times, unless it is deliberately moved by the user. This facilitates use, since the user may release insertion aid during use, without the risk of the insertion aid falling down and the like. It also facilitates manufacturing, since the insertion aid can hereby be arranged on the catheter already during manufacturing, and then remain in place during packaging, sterilization, handling, storage, etc. It will also remain in place during activation and preparation for use, e.g. when the catheter is removed from its package.

The insertion aid may also comprise inward protrusions or recessions which may be engaged with a recession or protrusion or the like in the catheter and/or catheter connector, thereby securely connecting the insertion aid to the catheter. Such a connection may form a weak mechanical interlocking, which maintains the insertion aid in an intended stored position. At the same time, disassembling of the insertion aid is simple, since the insertion aid can easily be pulled out of this weakly locked state, thereby allowing clean and safe maneuvering of insertion aid over the catheter during insertion into the intended human cavity. Further, the insertion aid will always be kept securely in place before it is removed and used as an insertion aid.

The insertion aid is preferably arranged overlying or adjacent the connector of the catheter. Thus, if the user does not need an insertion aid for manipulation of the catheter, the insertion aid can be allowed to remain in its non-released state during the entire use. Even in this way of using the catheter, where the insertion aid remains non-detached, the insertion aid is to advantage, since it hereby provides an enlarged gripping portion for the catheter, which makes insertion and withdrawal of the catheter easier, especially for users with reduced dexterity.

Pre-arrangement of the insertion aid on the catheter can be done with high speed automated manufacturing. The insertion aid can be mounted from the side, i.e. in a lateral direction seen from the catheter. Consequently, the need for pulling the insertion aid over the length of the catheter is avoided, which facilitates automated manufacturing.

Upon use, the insertion aid may be loosened from its storage position, if pre-arranged on the catheter, or alternatively be assembled over the catheter, if arranged separated from the catheter during storage.

Figure 9:
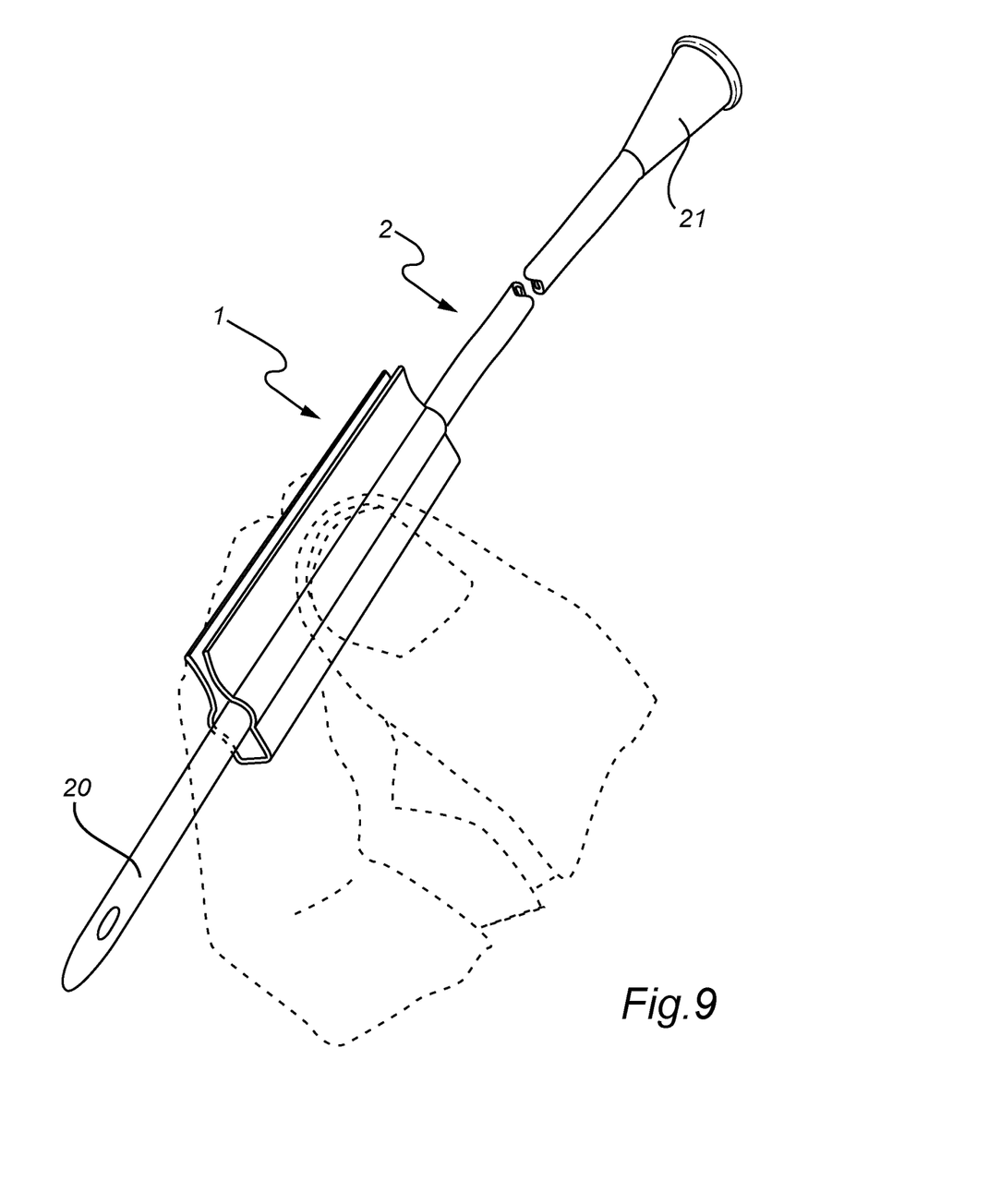
FIG. 9 is a side view in perspective of the insertion aid of FIG. 1 when being arranged on a catheter in a use position.

A catheter with an insertion aid arranged thereon is illustrated in FIG. 9. The catheter 2 comprises a forward insertion part 20 and a rearward connector part 21. The connector part may form a waist (not shown) having a cross-sectional dimension of lower extension than the surrounding portions of the connector part. In a preferred embodiment, the connector part 21 comprises a funnel shaped rearward end, tapering in a direction towards the insertion end of the catheter. However, other configurations of the rearward connector part 21 are also feasible, such as a cylindrical outer surface being provided with an indentation or similar waist, or other types of a non-circular circumference.

The forward insertion part 20 preferably comprises an elongate shaft with an insertion end. The insertion end is preferably provided with one or several drainage openings, in fluid communication with an internal lumen of the catheter.

The catheter may be of any size suitable for catheterization. For use by female users the elongate shaft preferably has a length in the range of 5-20 cm, such as in the size of 15 cm. For male users, the elongate shaft preferably has a length in the range 18-45 cm, such as in the size of 40 cm.

In order to further facilitate insertion of the catheter, the elongate shaft may comprise a hydrophilic material at the surface, said hydrophilic material providing a low-friction character to the catheter surface when wetted. For example, the elongate shaft can be made essentially entirely of a hydrophilic material. Alternatively, the elongate shaft may be provided with a hydrophilic surface coating.

The hydrophilic material may e.g. be polyvinyl pyrrolidone (PVP), but many other types of hydrophilic coatings are known in the art, and may be used in the context of the present disclosed technology. The hydrophilic coating provides a low-friction character to the catheter when wetted, thereby facilitating insertion of the catheter into the urethra, and reducing the risk of pain etc.

After arrangement of the insertion aid on the catheter shaft, as shown in FIG. 9, the insertion aid 1 is usable as an insertion aid for maneuvering the catheter 2 during insertion into the human cavity. In this position, the insertion aid 1 may be moved along the length of the elongate shaft, when no compression force is applied, and firmly fixate the catheter when a compression force is applied, thereby facilitating contamination free handling of the catheter, which reduces the risk of urinary tract infections and the like. Clamping can easily be obtained by pressing the plate-like arms towards each other. This can be made by pressing the plate-like arms together by use of two fingers, by means of pressing one or several fingers towards the palm, by use of two hands, by pressing on only one of the plate-like arms while the other is in contact with another part of the body or an external structure, and the like. Thus, the insertion aid provides numerous simple handling possibilities, which is particularly useful for users having reduced dexterity.

In this use position, the catheter 2 is positioned within the groove(s) of the insertion aid 1, so that the catheter is maintained in a correct position during operation, avoiding the risk of the catheter inadvertently falling out or being misplaced.

Due to the resilience, the insertion aid will apply a pressure on the enlarged rearward part (the connector) of the catheter, and it may consequently be held in place solely by friction. The user may choose not to use the insertion aid, and in such a case, the insertion aid will remain in its place, attached to connector, during the entire catheterization. If the user decides to use the insertion aid, the clip is easily pulled down from its attached position, and is then easily movable along the catheter shaft.

A method for producing a catheter assembly of this type includes:

Assembling a insertion aid of the above-discussed type on a catheter.

Arranging the catheter and, optionally a wetting fluid or a wetting fluid container, in a package.

Closing the package.

Sterilizing the package, including its content.

The disclosed technology has now been disclosed with reference to specific exemplary embodiments. However, it will be acknowledged by the skilled addressee that several modifications are possible. For example, various types of gripping means and the like may be provided, to facilitate gripping, various forms of ridges, surface texture or the like may be applied to the interior surface to increase friction, etc. Further, the insertion aid may be used for other types of catheters, e.g. catheters having differently designed connector ends, and the catheter set may also be arranged in many different forms of catheter assemblies.

The above-discussed and other obvious modifications must be considered to be within the scope of the disclosed technology. It should be noted that the above-mentioned embodiments illustrate rather than limit the disclosed technology, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. An insertion aid for catheter manipulation, comprising first and second plate-like arms arranged overlying each other and with a separation distance therebetween, and a resilient hinge connecting adjacent marginal edges of said plate-like arms together, wherein at least one of said plate-like arms is provided with a groove on a clamping inner surface thereof for holding a catheter shaft, the groove extending at least partly in the same direction as, and substantially parallel to, said resilient hinge, and distantly arranged from both the resilient hinge and from the marginal edge of said plate-like arm, the groove arranged between the resilient hinge and the marginal edge, and wherein the resilient hinge is arranged to exert a clamping force onto a catheter arranged in the insertion aid when in an unbiased state.

2. The insertion aid of claim 1, wherein the groove is arranged closer to the resilient hinge than to the marginal edge of said plate-like arm being opposite to said resilient hinge.

3. The insertion aid of claim 2, wherein a distance between the groove and the resilient hinge is 25% to 75% of a distance between the groove and the marginal edge of said plate-like arm being opposite to said resilient hinge.

4. The insertion aid of claim 2, wherein a distance between the groove and the resilient hinge is 30% to 70% of a distance between the groove and the marginal edge of said plate-like arm being opposite to said resilient hinge.

5. The insertion aid of claim 2, wherein a distance between the groove and the resilient hinge is 40% to 60% of a distance between the groove and the marginal edge of said plate-like arm being opposite to said resilient hinge.

6. The insertion aid of claim 1, wherein both of said plate-like arms are provided with the groove on a clamping inner surface thereof for holding the catheter shaft, the grooves being arranged overlying each other.

7. The insertion aid of claim 1, wherein the insertion aid includes has a length dimension in the direction of the resilient hinge which is longer than the width dimension perpendicular to the resilient hinge.

8. The insertion aid of claim 1, wherein the insertion aid includes has a length dimension in the direction of the resilient hinge which is at least 50% longer than the width dimension perpendicular to the resilient hinge.

9. The insertion aid of claim 1, wherein the insertion aid includes has a length dimension in the direction of the resilient hinge which is at least 100% longer than the width dimension perpendicular to the resilient hinge.

10. The insertion aid of claim 1, wherein the insertion aid is elongated in the direction of the groove, having a length that is in the range of 4 to 10 cm.

11. The insertion aid of claim 1, wherein the insertion aid is elongated in the direction of the groove, having a length is in the range of 5 to 9 cm.

12. The insertion aid of claim 1, wherein the insertion aid is elongated in the direction of the groove, having a length is in the range of 6 to 8 cm.

13. The insertion aid of claim 1, wherein the groove and the resilient hinge extend along straight, parallel lines.

14. The insertion aid of claim 1, wherein the plate-like arms are curved or bent away from each other along at least part of the marginal edge.

15. The insertion aid of claim 1, wherein the plate-like arm includes a slanted or beveled internal surface in the vicinity of the ends of the groove.

16. The insertion aid of claim 1, wherein at least one of the plate-like arms is provided with protrusions on an external surface thereof.

17. The insertion aid of claim 16, wherein each of the protrusions extend in a direction perpendicular to the groove.

18. The insertion aid of claim 1, wherein each of the plate-like arms is provided with a protrusion on an external surface thereof.

19. The insertion aid of claim 1, wherein at least one of the plate-like arms is provided with protrusions on an internal surface thereof.

20. The insertion aid of claim 19, wherein each of the protrusions extend in a direction perpendicular to the groove.

21. The insertion aid of claim 1, wherein each of the plate-like arms is provided with protrusions on an internal surface thereof.

22. The insertion aid of claim 1, wherein the insertion aid is formed as a clip, wherein the plate-like arms form a receiving mouth at the ends opposite to the resilient hinge.

23. The insertion aid of claim 1, wherein the insertion aid is monolithic and is formed from a material comprising a plastics material.

24. The insertion aid of claim 23, wherein the insertion aid is formed from a material that includes a thermoplastic and/or thermosetting plastic material.

25. The insertion aid of claim 23, wherein the insertion aid is formed from a material that includes a thermoplastic elastomer.

26. The insertion aid of claim 1, wherein the resilient hinge is provided with at least one cavity or opening arranged between the plate-like arms.

27. A catheter set comprising a catheter and the insertion aid of claim 1, wherein the catheter comprises a forward insertion part and a rearward connector part, wherein, in a storage position, the insertion aid is arranged over the connector part of the catheter so that the insertion aid detachably connects the insertion aid to the catheter.

28. The catheter set of claim 27, wherein the catheter is a hydrophilic catheter, and wherein the forward insertion part is at least partly provided with a hydrophilic material exhibiting low-friction surface properties when wetted.

29. The catheter set of claim 27, wherein the catheter is a urinary catheter.

30. The catheter set of claim 29, wherein the catheter is a urinary catheter for intermittent use.

31. The catheter set of claim 27, wherein the insertion aid is more rigid than the catheter shaft.

32. A catheter assembly comprising a catheter set of claim 27 and a package enclosing said catheter set.

* * * * *